(12) United States Patent
Spitzer et al.

(10) Patent No.: US 11,699,503 B2
(45) Date of Patent: Jul. 11, 2023

(54) METHODS OF IDENTIFYING AND TREATING PATIENT POPULATIONS AMENABLE TO CANCER IMMUNOTHERAPY

(71) Applicant: The Regents of the University of California, Oakland, CA (US)

(72) Inventors: Matthew Spitzer, San Francisco, CA (US); Lawrence Fong, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 7 days.

(21) Appl. No.: 16/479,211

(22) PCT Filed: Jan. 19, 2018

(86) PCT No.: PCT/US2018/014503
§ 371 (c)(1),
(2) Date: Jul. 18, 2019

(87) PCT Pub. No.: WO2018/136784
PCT Pub. Date: Jul. 26, 2018

(65) Prior Publication Data
US 2019/0378594 A1 Dec. 12, 2019

Related U.S. Application Data

(60) Provisional application No. 62/448,281, filed on Jan. 19, 2017.

(51) Int. Cl.
| | | |
|---|---|---|
| *G16B 25/10* | (2019.01) | |
| *G16B 5/10* | (2019.01) | |
| *G16B 45/00* | (2019.01) | |
| *A61K 38/19* | (2006.01) | |
| *A61K 39/395* | (2006.01) | |
| *C07K 16/28* | (2006.01) | |
| *G01N 33/50* | (2006.01) | |

(52) U.S. Cl.
CPC ............ *G16B 25/10* (2019.02); *A61K 38/193* (2013.01); *A61K 39/3955* (2013.01); *C07K 16/2818* (2013.01); *G01N 33/505* (2013.01); *G16B 5/10* (2019.02); *G16B 45/00* (2019.02); *G01N 2333/70596* (2013.01)

(58) Field of Classification Search
CPC ....... G01N 33/505; G01N 2333/70596; G01N 2800/52; G01N 33/5743; G01N 2333/7155; G16B 25/10; G16B 5/10; G16B 45/00
See application file for complete search history.

(56) References Cited

FOREIGN PATENT DOCUMENTS

| | | | |
|---|---|---|---|
| WO | WO-2014/153150 A1 | 9/2014 | |
| WO | WO-2016/164799 A1 | 10/2016 | |
| WO | WO-2016164799 A1 * | 10/2016 | ......... C07K 16/2818 |
| WO | WO-2016/191660 A1 | 12/2016 | |

OTHER PUBLICATIONS

Kwek et al. Preexisting Levels of CD4 T Cells Expressing PD-1 are Related to Overall Survival in Prostate Cancer Patients Treated with Ipilimumab. Cancer Immunol Res. Sep. 2015;3(9):1008-16 (Year: 2015).*
Guan etal.PD-L1 is a critical mediator of regulatory B cells and T cells in invasive breast cancer. Sci Rep 6, 35651 (2016) (Year: 2016).*
Kwek et al. GM-CSF and ipilimumab therapy in metastatic melanoma: Clinical outcomes and immunologic responses. Oncoimmunology 2016, vol. 5, No. 4, e1101204 (Year: 2016).*
Zhong et al. Expression of PD-1 by CD4+CD25+CD127low Treg cells in the peripheral blood of lung cancer patients. OncoTargets and Therapy 2015:8 1831-1833 (Year: 2015).*
Jacobs et al. Regulatory T cells and the PD-L1/PD-1 pathway mediate immune suppression in malignant human brain tumors. Neuro-Oncology 11, 394-402, 2009 (Year: 2009).*
Fujii et al. Biomarkers of response to immune checkpoint blockade in cancer treatment. Critical Reviews in Oncology/Hematology, 2018; 130:108-120 (Year: 2018).*
Paul. Fundamental Immunology, 3rd Edition, Raven Press, New York, Chapters, pp. 292-295, 1993 (Year: 1993).*
MacCallum et al. Antibody-antigen Interactions: Contact Analysis and Binding Site Topography. Journal of Molecular Biology, 262: 732-745, 1996 (Year: 1996).*
Vajdos et al. Comprehensive Functional Maps of the Antigen binding Site of an Anti-ErbB2 Antibody Obtained with Shotgun Scanning Mutagenesis. Journal of Molecular Biology, Jul. 5, 2002;320(2):415-28 (Year: 2002).*
Ferrara et al. Recombinant renewable polyclonal antibodies. mABs, 2015; 7(1): 32-41 (Year: 2015).*
Bair, E. et al. (Apr. 2004). "Semi-Supervised Methods to Predict Patient Survival from Gene Expression Data," *PLoS Biology* 2(4): e108.
Bandura, D.R. et al. (2009). "Mass cytometry: technique for real time single cell multitarget immunoassay based on inductively coupled plasma time-of- flight mass spectrometry," *Anal. Chem.* 81, 6813-6822.
Bates, G.J. et al. (Dec. 1, 2006). "Quantification of regulatory T cells enables the identification of high-risk breast cancer patients and those at risk of late relapse," *J Clin Oncol* 24(34):5373-5380.
Bendall, S.C. et al. (May 6, 2011). "Single-cell mass cytometry of differential immune and drug responses across a human hematopoietic continuum," *Science* 332(6030):687-696.

(Continued)

*Primary Examiner* — Vanessa L. Ford
*Assistant Examiner* — Sandra Carter
(74) *Attorney, Agent, or Firm* — Mintz, Levin, Cohn, Ferris, Glovsk (57) ABSTRACT

Methods for identifying cancer patients amenable to anti-cancer immunotherapy are provided along with methods of monitoring cancer therapy. Also provided are methods of treating cancer patients amenable to anti-cancer immunotherapy. The methods involve determining the level of CD127 <low> PD-1 <low> T cells. The patients are treated with an immune checkpoint inhibitor, such as an anti-CTLA-4 antibody, e.g. ipilimumab.

14 Claims, 5 Drawing Sheets

(56) References Cited

OTHER PUBLICATIONS

Bos, P.D. et al. (Oct. 21, 2013, e-published Oct. 14, 2013). "Transient regulatory T cell ablation deters oncogene-driven breast cancer and enhances radiotherapy," *J Exp Med* 210(11):2435-2466.

Broz, M.L. et al. (Nov. 10, 2014, e-published Oct. 16, 2014). "Dissecting the tumor myeloid compartment reveals rare activating antigen-presenting cells critical for T cell immunity," *Cancer Cell* 26(5):638-652.

Bruggner, R.V. et al. (Jul. 1, 2014, e-published Jun. 16, 2014). "Automated identification of stratifying signatures in cellular subpopulations," *PNAS USA* 111 (26):E2770-E2777.

Bulliard, Y. et al. (2013). Activating Fc γ receptors contribute to the antitumor activities of immunoregulatory receptor-targeting antibodies, *J Exp Med* 210(9):1685-1693.

Carmi, Y. et al. (May 7, 2015, e-published Apr. 29, 2015). "Allogeneic IgG combined with dendritic cell stimuli induce antitumor T-cell immunity," *Nature* 521(7550):99-104.

Cekic, C. et al. (Dec. 15, 2014, e-published Oct. 23, 2014,). "Adenosine A2A receptors intrinsically regulate CD8+ T cells in the tumor microenvironment," *Cancer Research* 74(24):7239-7249.

Chen, D.S. et al. (Jul. 25, 2013). "Oncology meets immunology: the cancer-immunity cycle," *Immunity* 39(1):1-10.

Cheng, G. et al. (Aug. 15, 2012, e-published Jul. 11, 2012). "IL-2 receptor signaling is essential for the development of Klrg1+ terminally differentiated T regulatory cells," *J Immunol* 189(4):1780-1791.

Cohen, C.J. et al. (Oct. 1, 2015, e-published Sep. 21, 2015). "Isolation of neoantigen-specific T cells from tumor and peripheral lymphocytes," *J Clin Invest* 125(10):3981-3991.

Coley, W.B. (1893). "The treatment of malignant tumors by repeated inoculations of erysipelas: with a report of ten original cases," *Am J Med Sci* 105(5):487-511.

Curiel, T.J. et al. (Sep. 2004, e-published Aug. 22, 2004). "Specific recruitment of regulatory T cells in ovarian carcinoma fosters immune privilege and predicts reduced survival," *Nat Med* 10(9):942-949.

Dankort, D. et al. (May 2009, e-published Mar. 12, 2009). "Braf$^{V600E}$ cooperates with Pten loss to induce metastatic melanoma," *Nat Genet* 41 (5):544-552.

Finck, R. et al. (May 2013, Mar. 19, 2013). "Normalization of mass cytometry data with bead standards," *Cytometry A* 83(5):483-494.

Gabrilovich, D.I. et al. (2012). "Coordinated regulation of myeloid cells by tumours," *Nat Rev Immunol* 12(4):253-268.

Haeryfar, S.M.M. et al. (Sep. 15, 2004). "Thy-1: more than a mouse pan-T cell marker," *J Immunol* 173(6):3581-3588.

Hanninen, A. et al. (Mar. 2011, e-published Feb. 10, 2011). "Ly6C supports preferential homing of central memory CD8+ T cells into lymph nodes," *Eur J Immunol* 41(3):634-644.

Herbst, R.S. et al. (Nov. 27, 2014). "Predictive correlates of response to the anti-PD-L1 antibody MPDL3280A in cancer patients," *Nature* 515(7528):563-567.

Hodi, F.S. et al. (Aug. 19, 2010, e-published Jun. 5, 2010). "Improved survival with ipilimumab in patients with metastatic melanoma," *N Engl J Med* 363(8):711-723.

Hodi, F.S. et al. (Nov. 5, 2014). "Ipilimumab plus sargramostim vs ipilimumab alone for treatment of metastatic melanoma: a randomized clinical trial," *JAMA* 312(17):1744-1753.

Ideker, T. et al. (Jan. 17, 2012). "Differential network biology," *Mol Syst Biol* 8:565.

Im, S.J. et al. (Sep. 15, 2016, e-published Aug. 2, 2016). "Defining CD8+ T cells that provide the proliferative burst after PD-1 therapy," *Nature* 537(7620):417-421.

International Search Report dated May 23, 2018, for PCT Application No. PCT/US2018/014503, filed Jan. 19, 2018, 5 pages.

Jiang, Y. et al. (Jun. 18, 2015). "T-cell exhaustion in the tumor microenvironment," *Cell Death Dis* 6:(6):e1792.

Kantoff, P.W. et al. (Jul. 29, 2010). "Sipuleucel-T immunotherapy for castration-resistant prostate cancer," *N Engl J Med* 363(5):411-422.

Kvistborg, P. et al. (Sep. 17, 2014). "Anti-CTLA-4 therapy broadens the melanoma-reactive CD8+ T cell response," *Sci Transl Med* 6(254):254ra128,10 pages.

Kwek, S.S. et al. (Sep. 2015, e-published May 12, 2015). "Preexisting Levels of CD4 T Cells Expressing PD-1 are Related to Overall Survival in Prostate Cancer Patients Treated with Ipilimumab," *Cancer Immunology Research* 3(9):1008-1016.

Kwek, S.S. et al. (Oct. 29, 2015, e-collection Apr. 2016). "GM-CSF and ipilimumab therapy in metastatic melanoma: Clinical outcomes and immunologic responses," *Oncoimmunology* 5(4):e1101204.

Matloubian, M. et al. (Jan. 22, 2004). "Lymphocyte egress from thymus and peripheral lymphoid organs is dependent on S1P receptor 1," *Nature* 427(6972):355-360.

McDermott, D. et al. (Oct. 2014, e-published Jul. 7, 2014). "Durable benefit and the potential for long-term survival with immunotherapy in advanced melanoma," *Cancer Treat Rev* 40(9):1056-1064.

Pelletier, N. et al. (Dec. 2010, e-published Oct. 31, 2010). "Plasma cells negatively regulate the follicular helper T cell program," *Nat Immunol* 11 (12):1110-1118.

Porter, D.L. et al. (Aug. 25, 2011, e-published Aug. 10, 2011). "Chimeric antigen receptor-modified T cells in chronic lymphoid leukemia," *N Engl J Med* 365(8):725-733.

Prieto, P.A. et al. (Apr. 1, 2012, e-published Jan. 23, 2012). CTLA-4 blockade with ipilimumab: long-term follow-up of 177 patients with metastatic melanoma, *Clin Cancer Res* 18(7):2039-2047.

Restifo, N.P. et al. (Mar. 22, 2012). "Adoptive immunotherapy for cancer: harnessing the T cell response," *Nat Rev Immunol* 12(4):269-281.

Robert, C. et al. (Jun. 30, 2011, e-published Jun. 5, 2011). "Ipilimumab plus dacarbazine for previously untreated metastatic melanoma," *N Engl J Med* 364(26):2517-2526.

Rosenberg, S.A. (Nov. 2014, e-published Oct. 14, 2014). "Decade in review-cancer immunotherapy: entering the mainstream of cancer treatment," *Nat Rev Clin Oncol* 11(11):630-632.

Simpson, T.R. et al. (Aug. 26, 2013, e-published Jul. 29, 2013). "Fc-dependent depletion of tumor-infiltrating regulatory T cells co-defines the efficacy of anti-CTLA-4 therapy against melanoma," *J Exp Med* 210(9):1695-1710.

Spitzer, M.H. et al. (Jul. 10, 2015). "Immunology. An interactive reference framework for modeling a dynamic immune system," *Science* 349(6244):1259425.

Spranger, S. et al. (Feb. 18, 2014). "Mechanism of tumor rejection with doublets of CTLA-4, PD-1/PD-L1, or IDO blockade involves restored IL-2 production and proliferation of CD8(+) T cells directly within the tumor microenvironment," *J Immunother Cancer* 2:3.

Swain, S.L. et al. (Jan. 20, 2012). "Expanding roles for CD4+ T cells in immunity to viruses," *Nat Rev Immunol* 12(2):136-148.

Topalian, S.L. et al. (Apr. 13, 2015, e-published Apr. 6, 2015). "Immune checkpoint blockade: a common denominator approach to cancer therapy," *Cancer Cell* 27(4):450-461.

Tran, E. et al. (May 9, 2014). "Cancer immunotherapy based on mutation-specific CD4+ T cells in a patient with epithelial cancer," *Science* 344(6184):641-645.

Wherry, E. J. et al. (Oct. 2007, e-published Oct. 18, 2007). "Molecular signature of CD8+ T cell exhaustion during chronic viral infection," *Immunity* 27(4):670-684.

Written Opinion dated May 23, 2018, for PCT Application No. PCT/US2018/014503, filed Jan. 19, 2018, 6 pages.

Xie, Y. et al. (Mar. 15, 2010, e-published Feb. 15, 2010). "Naive tumor-specific CD4(+) T cells differentiated in vivo eradicate established melanoma," *J Exp Med* 207(3):651-667.

Zunder, E.R. et al. (Feb. 2015, e-published Jan. 22, 2015). "Palladium-based mass tag cell barcoding with a doublet-filtering scheme and single-cell deconvolution algorithm," *Nat Protoc* 10(2):316-333.

\* cited by examiner

METHODS OF IDENTIFYING AND TREATING PATIENT POPULATIONS AMENABLE TO CANCER IMMUNOTHERAPY

CROSS REFERENCE TO RELATED APPLICATIONS

This application is a national stage entry, filed under 35 U.S.C. § 371, of International Application No. PCT/US2018/014503, filed Jan. 19, 2018, which claims the benefit of priority to U.S. Provisional Application No. 62/448,281, filed Jan. 19, 2017; the contents of each of which are incorporated herein by reference in their entirety and for all purposes.

STATEMENT OF GOVERNMENT SUPPORT

This invention was made with government support under W81XWH-12-1-0591 awarded by the Medical Research and Development Command, OD023056, U19 AI100627, R33 CA183654, R01 AI118884, R01 CA196657, U19 AI057229, R01 HL120724, and HHSN272201200028C awarded by the National Institutes of Health, and HHSF223201210194C awarded by the Food and Drug Administration. The government has certain rights in the invention.

BACKGROUND

Since the use of bacterial vaccines for the treatment of cancer over a century ago (Coley, 1893), evidence has mounted demonstrating the ability of the immune system to reject tumors. Several immunotherapeutic strategies have now yielded sustained clinical responses, including blocking antibodies against suppressive receptors (Topalian et al., 2015) and transfer of adoptive T cells (Restifo et al., 2012), dendritic cells (Kantoff et al., 2010), or engineered T cells (Porter et al., 2011). For specific immunotherapies, individual cell subsets have been queried for mechanistic roles, and features have been correlated with responsiveness (Herbst et al., 2014). A comprehensive understanding of the global immune dynamics that mediate effective anti-tumor immunity remains unclear, however. Because most cancer patients do not respond to conventional immunotherapy, there is an urgent need to improve upon the current toolkit, especially for adenocarcinomas, the most common forms of cancer.

Another gap in our knowledge is where anti-tumor immunity is fostered anatomically. Expansion of tumor-infiltrating T cells has shown striking results in melanoma, demonstrating that effective cells can be found within the microenvironment (Restifo et al., 2012). In contrast, dendritic cell vaccines can stimulate de novo T cell responses and have shown efficacy (Kantoff et al., 2010). For strategies that initiate anti-tumor immunity in the patient, it remains unclear where immune cell activation takes place. For example, in the case of CTLA-4 blockade, administering antibody into the tumor can induce rejection (Simpson et al., 2013) and is dependent on Fcy receptors (Bulliard et al., 2013), consistent with depleting intratumoral regulatory T cells and releasing local effector cells. New tumor-reactive T cell clones emerge in patients experiencing clinical benefit, however, consistent with new priming (Kvistborg et al., 2014). For other strategies to induce immune responses in situ, this question has not been addressed conclusively.

T-cells or T lymphocytes play a central role in cell-mediated immunity. They can be distinguished from other lymphocytes by the presence of a T-cell receptor (TCR) on the cell surface. T-cells mature in the thymus (although some also mature in the tonsils). There are several types of T cells, and each type has a distinct function. The various types of T-cells include T Helper cells (TH cells), cytotoxic T-cells (CTLs), multiple sub-types of Memory T-cells, effector T cells ($T_{eff}$), regulatory T-cells ($T_{reg}$), and Natural Killer T-cells (NKT cells).

T helper cells (TH cells) assist in the maturation of B cells into plasma cells and memory B cells, as well as in the activation of cytotoxic T cells and macrophages. These $T_H$ cells, also known as CD4$^+$ T-cells, express the CD4 glycoprotein on their surfaces. Helper T-cells become activated when they are presented with peptide antigens by MHC class II molecules, which are expressed on the surface of antigen-presenting cells or APCs. Once activated, Helper T-cells divide and secrete cytokines that regulate the active immune response.

Cytotoxic T-lymphocyte antigen-4 (CTLA-4) is an immune checkpoint receptor expressed on T cells that mediate inhibitory immune responses in the early activation of naive and memory T cells to maintain a balanced immune homeostasis (1) (2). CTLA-4 is found on the surface of T cells, which are involved in the cellular immune response to foreign antigen. T-cells can be activated by stimulating the CD28 receptor on the T-cell. T-cells can be inhibited by stimulating the CTLA-4 receptor, which acts as an "off" switch. CTLA-4 is a member of the immunoglobulin superfamily, which is expressed on the surface of Helper T cells and transmits an inhibitory signal to T cells. CTLA-4 is similar to the T-cell co-stimulatory protein, CD28, and both molecules bind to CD80 and CD86, also called B7-1 and B7-2 respectively, on antigen-presenting cells. In contrast to the stimulatory signal transmitted by CD28, CTLA-4 transmits an inhibitory signal to T-cells. T-cell activation through the T-cell receptor and CD28 leads to increased expression of CTLA-4, an inhibitory receptor for B7 molecules.

Programmed death 1 (PD-1) is a type I membrane protein of 268 amino acids. PD-1 appears to negatively regulate immune responses, based on PD-1 knockout mice developing lupus-like glomerulonephritis and dilated cardiomyopathy in C57BL/6 and BALB/c genetic backgrounds, respectively. T-cells stimulated by exposure to an anti-CD3 antibody that are exposed to a ligand of PD-1 (i.e., PD-L1) exhibit reduced T cell proliferation and IFN-γ secretion. These data indicate that PD-1 negatively regulates T-cell responses.

Programmed death-ligand 1 (PD-L1, CD274, B7-H1) is a type I membrane protein of 176 amino acids. PD-L1 is expressed on antigen-presenting cells (APCs), activated T cells, and a variety of tissues. PD-L1 knockout mice demonstrated increased CD4 and CD8 T cell responses including increased levels of cytokines. This data suggests that PD-L1 negatively regulates T cells and play a role in T cell tolerance.

CD127 is the alpha chain of the Interleukin-7 Receptor protein that is found on a number of cell types, including naive and memory effector T cells. The IL-7 Receptor, comprised of CD127 α-chain and the CD132 common γ-chain, is believed to play a role in the development of lymphocytes by blocking apoptosis and is implicated in some forms of leukemia, some forms of arthritis, and multiple sclerosis.

The foregoing aspects of the immune system and the many other aspects of the immune system have been extensively studied for years as biologists and medical professionals have recognized the role played by the immune system in resisting disease and in combatting infection. Efforts to harness the considerable potential of the immune system to treat or prevent disease have led to the development of a number of biologics showing promise in the clinic. Those efforts, however, have required significant capital input and time expenditures due to care that can be taken in developing a treatment for humans, the number of failures, and the uneven response profiles of patients receiving treatment.

For all of the foregoing reasons, a need continues to exist in the art for materials and methods that yield effective methodologies for identifying cancer patients amenable to anti-cancer immunotherapy, for monitoring the treatment of such patients, and for treating patients amenable to anti-cancer immunotherapy.

SUMMARY

Disclosed herein are methods of assessing the immune state under any given condition to allow the systematic characterization of diverse cell subsets and their activation states simultaneously. Mass cytometry builds upon the success of flow cytometry and enables over 40 simultaneous parameters to be quantified by replacing fluorophores with mass tags (Bandura et al., 2009; Bendall et al., 2011). It is thus possible to discern the identity and behavior of numerous cell types from a single experiment (Bendall et al., 2011; Spitzer et al., 2015).

One aspect of the disclosure provides a method of identifying a patient population amenable to anti-cancer immunotherapy comprising: (a) measuring the level of $CD127^{low}$ $PD-L1^{low}$ T cells in a human cancer patient; (b) measuring the level of $CD127^{low}PD-L1^{low}$ T cells in a control, wherein the control is the human cancer patient at an earlier time or a healthy human; and (c) identifying the patient as amenable to anti-cancer immunotherapy if the level of $CD127^{low}$ $PD-L1^{low}$ T cells is higher in the patient than the level of $CD127^{low}$ $PD-L1^{low}$ T cells in the control. As used herein, $CD127^{low}$ $PD-L1^{low}$ CD4 T cells are CD4 T cells expressing both CD127 and PD-1 at levels below the median expression level of both CD127 and PD-1 for all CD4 T cells. A higher level of $CD127^{low}$ $PD-L1^{low}$ T cells means there is a greater level of such cells than found in a reference or control. The control is a sample from the cancer patient at a different point in time, such as an earlier point in time, such as prior to any cancer treatment. The control may also be a sample obtained from a healthy individual. The greater level is a detectably increased level of $CD127^{low}$ $PD-1^{low}$ T cells relative to the reference or control. In some embodiments, the T cells are CD4 cells, such as regulatory T cells. In some embodiments, the control is the human cancer patient at an earlier time, such as wherein the time is prior to a cancer treatment. In some embodiments, the cancer patient has melanoma. Embodiments are also envisaged wherein the patient has a tumor and the T cells are obtained intratumorally, or wherein the T cells are obtained from a secondary lymphoid organ or from peripheral blood.

Another aspect of the disclosure is a method of monitoring anti-cancer immunotherapy in a patient comprising: (a) measuring the level of $CD127^{low}$ $PD-1^{low}$ T cells in a human cancer patient; (b) measuring the level of $CD127^{low}$ $PD-1^{low}$ T cells in a control, wherein the control is the human cancer patient at an earlier time or a healthy human; and (c) identifying the patient as responding to anti-cancer immunotherapy if the level of $CD127^{low}$ $PD-1^{low}$ T cells is higher in the patient than the level of $CD127^{low}$ $PD-1^{low}$ T cells in the control. In some embodiments, the T cells are CD4 cells, such as regulatory T cells. In some embodiments, the control is the human cancer patient at an earlier time, such as wherein the time is prior to a cancer treatment. In some embodiments, the cancer patient has melanoma. Also contemplated are embodiments in which the patient has a tumor and the T cells are obtained intratumorally, or the T cells are obtained from a secondary lymphoid organ or from peripheral blood.

Yet another aspect of the disclosure is drawn to a method of treating cancer in a patient comprising administering a therapeutically effective amount of a composition comprising an immune checkpoint inhibitor and a soluble growth factor to a human patient with a higher level of $CD127^{low}$ $PD-1^{low}$ cells than a control, wherein the control is the human cancer patient at an earlier time or a healthy human, thereby treating the cancer in the patient. In some embodiments, the soluble growth factor is granulocyte-macrophage colony stimulating factor (GM-CSF). In some embodiments, the T cells are CD4 cells, such as regulatory T cells. In some embodiments, the control is the human cancer patient at an earlier time, such as wherein the time is prior to a cancer treatment. In some embodiments, the treatment inhibits the growth of cancer cells in the patient, and in some embodiments, the treatment inhibits the migration of cancer cells in the patient. Also included within this aspect of the disclosure are methods wherein the cancer patient has melanoma. In some embodiments, the immune checkpoint inhibitor is an anti-CTLA-4 antibody, an anti-CTLA-4 antibody fragment that binds CTLA-4, an anti-PD-1 antibody, an anti-PD-1 antibody fragment that binds PD-1, an anti-PD-L1 antibody, or an anti-PD-L1 antibody fragment that binds PD-L1. An exemplary immune checkpoint inhibitor suitable for use in this aspect of the disclosure is ipilimumab.

Other features and advantages of the present disclosure will become apparent from the following detailed description, including the drawing. It should be understood, however, that the detailed description and the specific examples are provided for illustration only, because various changes and modifications within the spirit and scope of the invention will become apparent to those skilled in the art from the detailed description.

Disclosed herein is a method of identifying a human cancer subject amenable to an anti-cancer immunotherapy, comprising: obtaining a dataset comprising data representing the level of $CD127^{low}$ $PD-1^{low}$ T cells in the human cancer subject; obtaining a dataset comprising data representing the level of $CD127^{low}$ $PD-1^{low}$ T cells in a control, wherein the control is the human cancer patient at an earlier time, a distinct human cancer subject that is unresponsive to the anti-cancer immunotherapy, or a healthy human; and assessing the amenability of the human cancer subject to the anti-cancer immunotherapy based on the data, optionally, identifying the human cancer subject as amenable to anti-cancer immunotherapy when the level of $CD127^{low}$ $PD-1^{low}$ T cells is greater in the human cancer subject than the level of $CD127^{low}$ $PD-1^{low}$ T cells in the control.

In some aspects, the method comprises: obtaining a dataset comprising data representing the level of $CD4^+$ $CD127^{low}$ $PD-1^{low}$ T cells in the human cancer subject; obtaining a dataset comprising data representing the level of $CD4^+$ $CD127^{low}$ $PD-1^{low}$ T cells in the control; identifying the subject as amenable to anti-cancer immunotherapy when the level of $CD4^+$ $CD127^{low}$ $PD-1^{low}$ T cells is greater in the human cancer subject than the level of $CD4^+$ $CD127^{low}$ PD-1$^{low}$ T cells in the control; and treating the human cancer subject with an anti-CTLA4 antibody.

In some aspects, the method further comprises treating the human cancer subject with an anti-CTLA4 antibody, optionally ipilimumab.

In some aspects, the method further comprises treating the human cancer subject with an anti-cancer immunotherapy, optionally an immune checkpoint inhibitor, and optionally the immune checkpoint inhibitor is an anti-CTLA-4 antibody, an anti-CTLA-4 antibody fragment that binds CTLA-4, an anti-PD-1 antibody, an anti-PD-1 antibody fragment that binds PD-1, an anti-PD-L1 antibody, or an anti-PD-L1 antibody fragment that binds PD-L1.

In some aspects, the method further comprises identifying the human cancer subject as amenable to anti-cancer immunotherapy when the level of CD127$^{low}$ PD-1$^{low}$ T cells is greater in the human cancer subject than the level of CD127$^{low}$ PD-1$^{low}$ T cells in the control.

In some aspects, T cells are CD4 positive cells. In some aspects, CD4 positive cells are regulatory T cells, optionally CD4$^+$CD25$^+$ regulatory T cells. In some aspects, the control is the human cancer subject at an earlier time. In some aspects, the time is prior to a cancer treatment. In some aspects, the cancer is melanoma. In some aspects, the human cancer subject has a tumor and the T cells are obtained intratumorally. In some aspects, T cells are obtained from a secondary lymphoid organ or from peripheral blood.

In some aspects, obtaining the dataset comprises receiving the dataset from a third party. In some aspects, obtaining the dataset comprises processing a sample from the human cancer subject and/or control to experimentally determine the dataset. In some aspects, processing comprises use of flow cytometry.

Also disclosed herein is a method of monitoring anti-cancer immunotherapy in a human cancer subject comprising: obtaining a dataset comprising data representing the level of CD127$^{low}$ PD-1$^{low}$ T cells in the human cancer subject; obtaining a dataset comprising data representing the level of CD127$^{low}$ PD-1$^{low}$ T cells in a control, wherein the control is the human cancer subject at an earlier time, a distinct human cancer subject that is unresponsive to anti-cancer immunotherapy, or a healthy human, wherein a greater level of CD127$^{low}$ PD-1$^{low}$ T cells in the human cancer subject relative to control is indicative of a response to the anti-cancer immunotherapy; and/or a lower level of CD127$^{low}$ PD-1$^{low}$ T cells in the human cancer subject relative to control is indicative of a lack of response to the anti-cancer immunotherapy.

In some aspects, T cells are CD4 positive cells. In some aspects, CD4 positive cells are regulatory T cells, optionally CD4$^+$CD25$^+$ regulatory T cells. In some aspects, the control is the human cancer subject at an earlier time. In some aspects, the time is prior to a cancer treatment. In some aspects, the cancer is melanoma. In some aspects, the human cancer subject has a tumor and the T cells are obtained intratumorally. In some aspects, T cells are obtained from a secondary lymphoid organ or from peripheral blood.

In some aspects, obtaining the dataset comprises receiving the dataset from a third party. In some aspects, obtaining the dataset comprises processing a sample from the human cancer subject and/or control to experimentally determine the dataset. In some aspects, processing comprises use of flow cytometry.

Also disclosed herein is a method of treating cancer in a human cancer subject comprising: administering a therapeutically effective amount of a composition comprising an immune checkpoint inhibitor to the subject, wherein the human cancer subject has been determined to have a greater level of CD127$^{low}$ PD-1$^{low}$ cells than a control, wherein the control is the human cancer subject at an earlier time, a distinct human cancer subject that is unresponsive to anti-cancer immunotherapy, or a healthy human, thereby treating the cancer in the human cancer subject, optionally further comprising administering a soluble growth factor to the human cancer subject.

In some aspects, the method further comprising determining that the human cancer subject has a greater level of CD127$^{low}$ PD-1$^{low}$ cells than the control prior to treatment with the immune checkpoint inhibitor, optionally wherein the inhibitor is an anti-CTLA4 antibody.

In some aspects, the method further comprises administering a soluble growth factor to the human cancer subject. In some aspects, a soluble growth factor is granulocyte-macrophage colony stimulating factor (GM-CSF). In some aspects, determining comprises receiving, from a third party, a dataset comprising data representing the level(s) of CD127$^{low}$ PD-1$^{low}$ cells. In some aspects, determining comprises processing a sample from the human cancer subject and/or control to experimentally determine a dataset comprising data representing the level(s) of CD127$^{low}$ PD-1$^{low}$ cells. In some aspects, processing comprises use of flow cytometry.

In some aspects, T cells are CD4 positive cells. In some aspects, CD4 positive cells are regulatory T cells, optionally CD4$^+$CD25$^+$ regulatory T cells. In some aspects, the control is the human cancer subject at an earlier time. In some aspects, the time is prior to a cancer treatment. In some aspects, the cancer is melanoma. In some aspects, the human cancer subject has a tumor and the T cells are obtained intratumorally. In some aspects, T cells are obtained from a secondary lymphoid organ or from peripheral blood.

In some aspects, treatment inhibits the growth of cancer cells. In some aspects, treatment inhibits the migration of cancer cells.

In some aspects, an immune checkpoint inhibitor is an anti-CTLA-4 antibody, an anti-CTLA-4 antibody fragment that binds CTLA-4, an anti-PD-1 antibody, an anti-PD-1 antibody fragment that binds PD-1, an anti-PD-L1 antibody, or an anti-PD-L1 antibody fragment that binds PD-L1. In some aspects, the immune checkpoint inhibitor is ipilimumab.

Also disclosed herein is a composition comprising: (a) a sample from a human cancer subject comprising T cells; (b) an anti-CD127 antibody; and (c) an anti-PD-1 antibody; optionally wherein the sample is from a tumor, a secondary lymphoid organ, and/or peripheral blood of the subject.

In some aspects, sample is from a tumor, a secondary lymphoid organ, and/or peripheral blood of the subject. In some aspects, T cells in the sample are CD4$^+$. In some aspects, T cells in the sample are CD127$^{low}$ PD-1$^{low}$, optionally as determined by flow cytometry. In some aspects, the cancer is melanoma. In some aspects, the antibodies are each bound to a single T cell. In some aspects, each of the antibodies are distinctly labeled with one or more detectable labels. In some aspects, the composition further comprises a buffer.

Also disclosed herein is a device, optionally a flow cytometry device, comprising a composition disclosed herein, optionally wherein the device is configured to detect antibodies of the composition.

BRIEF DESCRIPTION OF THE DRAWINGS

FIG. 1. The Statistical Scaffold algorithm. FIG. 1 (A) Scaffold maps as originally designed (Spitzer et al., 2015).

(i) A reference sample (or group thereof) is chosen for the analysis. (ii) Canonical cell populations are identified manually and all cells are also clustered in an unsupervised manner. (iii) Canonical populations are represented as landmark nodes, while clusters are represented as unsupervised nodes. (iv) These nodes are spatialized into a force-directed graph. (v) Landmark nodes are fixed in place to provide common reference points. (vi) Cells from other samples are clustered independently and (viii) graphs are generated for each sample. FIG. 1 (B) Statistical Scaffold. (i-ii) A set of reference samples is chosen and canonical cell populations as performed previously. However, all samples are clustered together. (iii-iv) Same as above. (v) Features (i.e., population frequencies, expression levels in each cluster, and the like) are extracted from the clusters for each sample. Each sample is also annotated according to the therapy to which it belongs. (vi) Significance Analysis of Microarrays is performed to identify features that are statistically significant between treatment groups. (vii) Features displaying statistically significant differences between groups are colored according to the direction of the change (increase or decrease) in the Scaffold maps to visualize which parts of the immune system are impacted by therapy.

FIG. 3 (A) Scaffold map of flow cytometry data from blood of melanoma patients treated with anti-CTLA-4 antibodies and GM-CSF, 3 weeks after therapy began. Red nodes are cell subsets significantly expanded in responding patients compared to non-responders. FIG. 3 (B) Frequency of $CD4^+$ $PD-1^{low}$ $CD127^{low}$ T cells (identified manually) of total leukocytes, analyzed by two-tailed Wilcoxon rank-sum test.

FIG. 4 (A) Statistical Scaffold map highlighting differences in peripheral blood immune cell frequencies between responding and non-responding melanoma patients 6 weeks after anti-CTLA-4 and GM-CSF immunotherapy. FIG. 4 (B) Histograms comparing the protein expression profiles of those CD4 T cell clusters that were significantly different in frequency between responders and non-responders at week 3 and the remainder of the CD4 T cell subsets that were not significantly different in frequency between these patient populations.

DETAILED DESCRIPTION

Immune responses involve coordination across cell types and tissues. While cancer immunotherapies can be effective, their mechanisms of action have never been characterized system-wide. For instance, cytotoxic T-lymphocyte-associated antigen 4 (CTLA-4) blockade can induce tumor regression and improve survival in cancer patients. This treatment can enhance adaptive immune responses without an exogenous vaccine, but the immunologic parameters associated with improved clinical outcome are not established. Ipilimumab is a fully humanized monoclonal antibody targeting CTLA-4 that is FDA-approved for the treatment of melanoma. In two phase III studies in advanced melanoma, ipilimumab was shown to significantly prolong overall survival (OS) (Hodi et al., 2010 and Robert et al. 2011). In the pivotal trial, melanoma patients were treated with ipilimumab plus gp100 (a melanoma peptide vaccine), ipilimumab alone, or gp100 alone (Hodi et al., 2010). The median overall survivals were 10.0, 10.1, and 6.4 months respectively. Although improvement in median overall survival was modest, a subset of patients was observed in these and other melanoma clinical trials to have durable long-term survival benefit (Prieto et al. 2012 and McDermott et al. 2014).

Disclosed herein is an emergent population of peripheral CD4 T cells that conferred protection against tumors and was significantly expanded in patients who responded to immunotherapy. Those cells are $CD127^{low}$ $PD-1^{low}$ CD4 T cells. $CD127^{low}$ $PD-1^{low}$ CD4 T cells are CD4 T cells expressing both CD127 and PD-1 at levels below the median expression levels of the respective markers (i.e., CD127 and PD-1) for all CD4 T cells. Measurement of the expression level of each of these markers, i.e., CD127 and PD-1, can be accomplished using any method known in the art. For example, the expression level of CD127 and/or PD-1 can be determined using flow cytometry or any of several assays, including real-time quantitative polymerase chain reaction (RT-qPCR), and immunoassays including enzyme-linked immunosorbent assay (ELISA), BIAcore assays (plasmon resonance-based assays), radioimmunoassays, and non-immunological binding assays, as would be known in the art. Many of these assays are readily adapted to assays on solid surfaces, including chip-based or micro-array assay formats. Samples to be subjected to such assays can be blood samples obtained from peripheral blood or the serum obtained from such blood, secondary lymphoid organ samples (e.g., spleen, lymph node), or tumor samples. Markers for identifying CD4 T cells are known in the art, and include, e.g., CD4 and CD3 as well as additional markers (e.g., one or more of CD25, CD45RA, CD45RO, CCR7, and/or C62BL) that may be used to differentiate CD4 T cell sub-types. A higher level of the $CD127^{low}$ $PD-1^{low}$ T cells means that there is a greater level of such cells in the sample being measured, and in the patient from whom the sample was obtained, than found in a reference or control. The control is a sample from the cancer patient at a different point in time, such as an earlier point in time, e.g., prior to any cancer treatment. The control may also be a sample obtained from a healthy individual. The greater level is a detectably increased level of $CD127^{low}$ $PD-1^{low}$ T cells relative to the reference or control. The approach disclosed herein identifies mechanisms of adaptive resistance systemically and in distal tumors that could be targeted to rationally augment immune responses, highlighting the utility of systems-level investigation.

New methods of assessing the immune state under any given condition allow for the systematic characterization of diverse cell subsets and their activation states simultaneously. Mass cytometry builds upon the success of flow cytometry and enables over 40 simultaneous parameters to be quantified by replacing fluorophores with mass tags (Bandura et al., 2009; Bendall et al., 2011). It is thus possible to discern the identity and behavior of numerous cell types from a single experiment (Bendall et al., 2011; Spitzer et al., 2015).

The variance in clinical responses to immunotherapy suggests that productive immune responses against cancer are necessarily complex. There is an urgent need for methods to understand the nature of anti-tumor immunity to more reproducibly harness the immune system against cancer.

Disclosed herein is a system-wide, organism-wide assessment of effective anti-tumor immune responses. Even for a therapy delivered intratumorally, a systemic immune response can be desirable for tumor rejection. With the increased use of immunotherapies, systemic responses can typically be taken into account when determining radiation or surgical regimens including lymphadenectomy.

Many studies have focused on CD4 T cells (Chen and Mellman, 2013; Im et al., 2016), with less emphasis on harnessing CD4 T cells (Tran et al., 2014; Xie et al., 2010). In other contexts, CD4 T cells orchestrate functional immune responses by coordinating immune activity (Swain et al., 2012). The results disclosed herein extend this notion to anti-tumor immunity, providing a rationale for leveraging CD4 T cell responses in cancer.

These results highlight the benefit of system-wide assessments. Simple prognostic metrics have been proposed for monitoring anti-tumor immunity, including Treg frequency in tumors (Bates et al., 2006; Curiel et al., 2004). Productive immunity in this setting is accompanied by an increase in Treg frequency and proliferation in the context of a powerful T cell response. With high throughput and high dimensional single-cell technologies such as mass cytometry, assessing all immune cells simultaneously is now achievable, enabling individual metrics to be contextualized into the broader immune state. For instance, the systemic proliferative response identified may provide a means for noninvasive monitoring during immunotherapy. The graphical user interface that accompanies Scaffold maps (GitHub) facilitates the application of the methods disclosed herein to the treatment and monitoring of a wide variety of cancers.

EXAMPLES

The following examples illustrate embodiments of the disclosure. Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Cell Cluster Mapping

Scaffold Map Generation

Figure 1A:
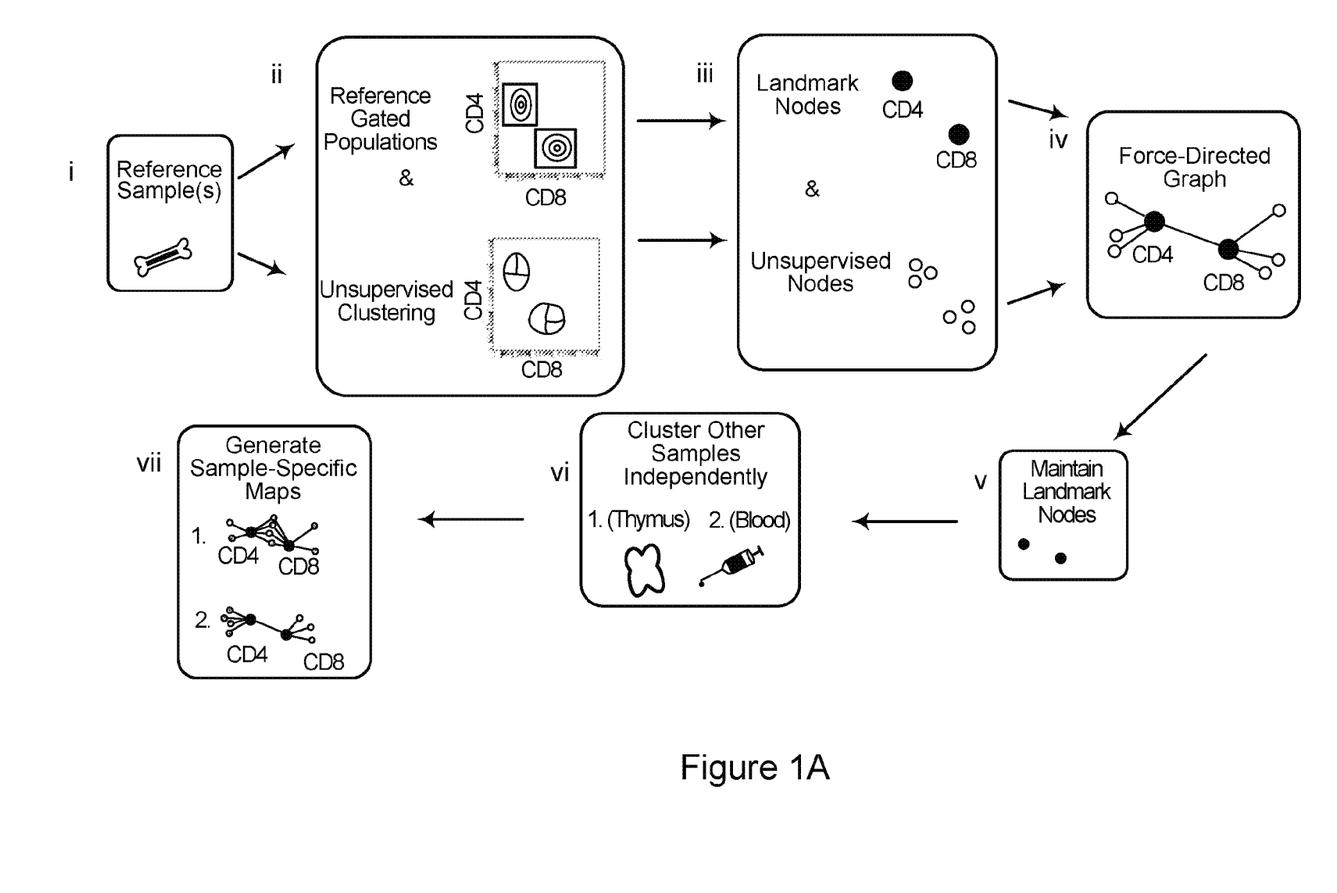
Figure 1B:
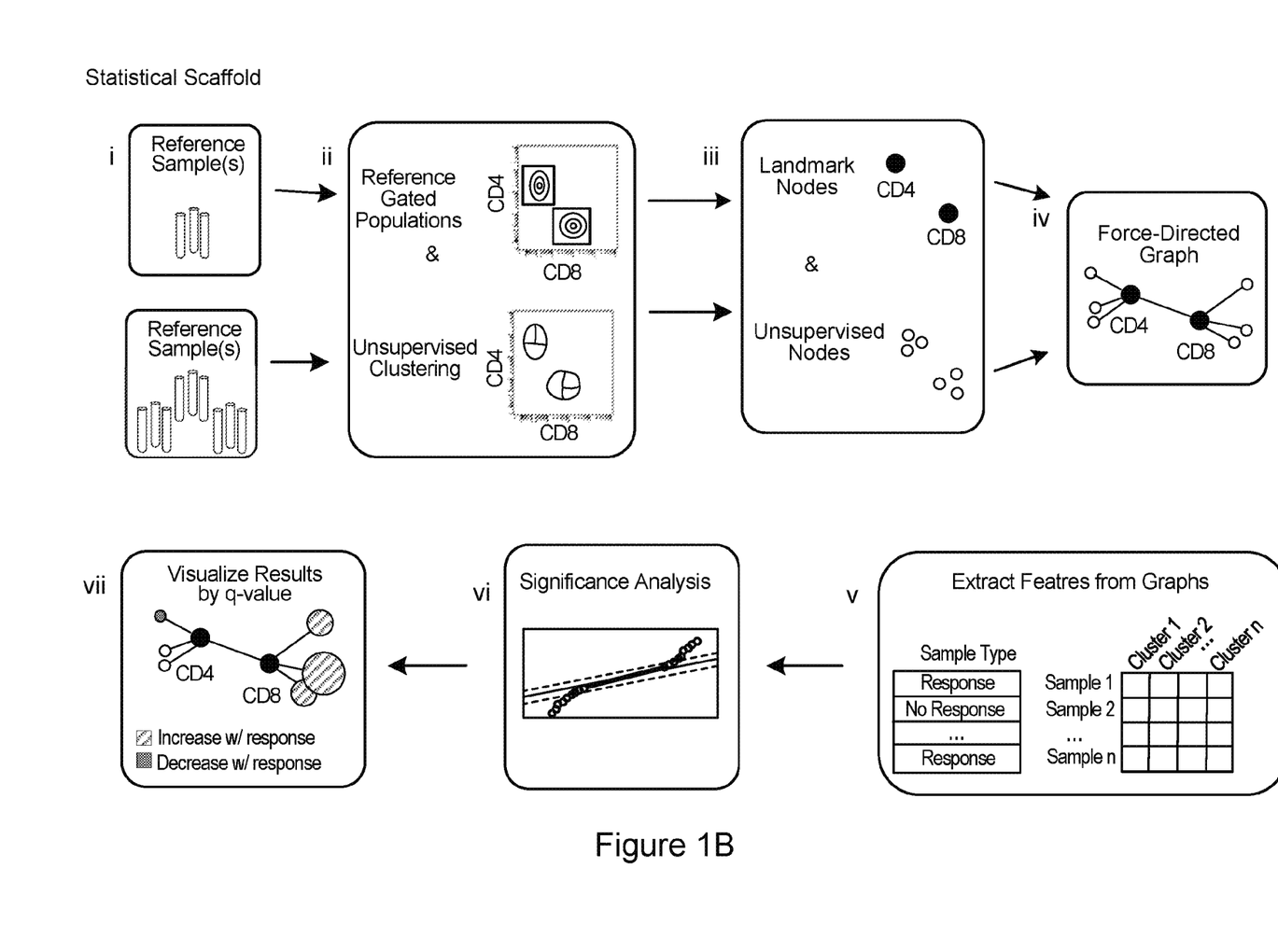

Total live leukocytes (excluding erythrocytes) are suitable for use in the analyses, schematically illustrated in FIG. 1. Cells from each tissue were clustered together (rather than performing CLARA clustering on each file individually as originally implemented in Spitzer et al., Science, 2015.) Cells were then deconvolved into their respective samples. Cluster frequencies or the Boolean expression of Ki67 or PD-L1 for each cluster were passed into the Significance Across Microanays algorithm (Bair and Tibshirani, 2004; Bruggner et al., 2014), and results were tabulated into the Scaffold map files for visualization through the graphical user interface. Cluster frequencies were calculated as a percent of total live nucleated cells (excluding erythrocytes). For each cluster in each tissue, the most similar cluster in every other tissue was included for comparison.

Figure 2:
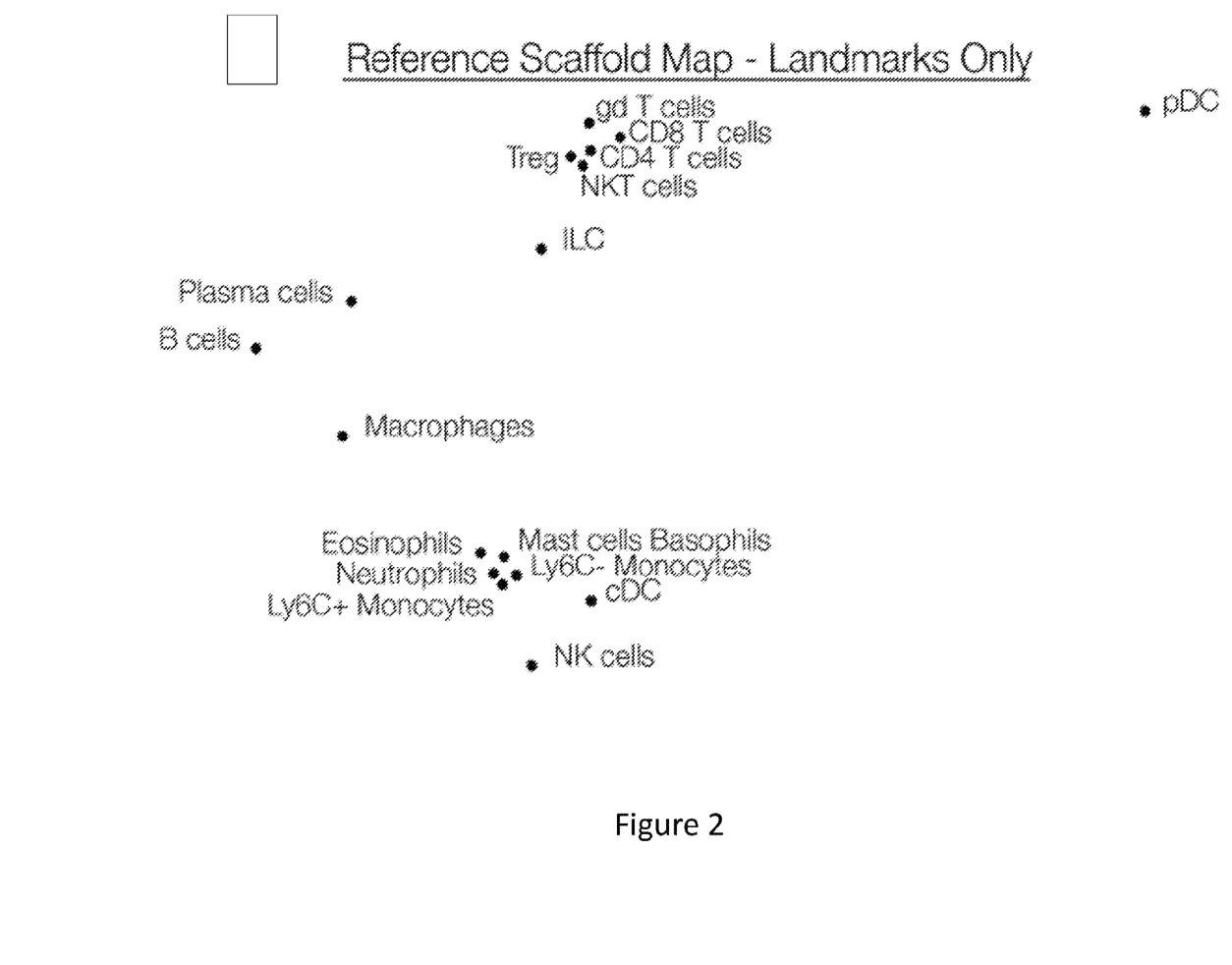
FIG. 2. Architecture of the Scaffold map. An empty Scaffold map displaying landmarks alone is presented for orientation.

Scaffold maps were then generated as previously reported (Spitzer et al., 2015). See FIG. 2 for an example of the architecture of a Scaffold map. A graph was constructed by first connecting together the nodes representing the manually gated landmark populations and then connecting to them the nodes representing the cell clusters as well as connecting the clusters to one another. Each node was associated with a vector containing the median marker values of the cells in the cluster (unsupervised nodes) or gated populations (landmark nodes). Edge weights were defined as the cosine similarity between these vectors after comparing the results from the implementation of several distance metrics. Edges of low weight were filtered out. The graph was then laid out using an in-house R implementation of the ForceAtlas2 algorithm from the graph visualization software Gephi. To overlay the additional samples on the map, the position and identity of the landmark nodes were fixed and the clusters of each sample were connected to the landmark nodes as described above. Once again the graphs were laid out using ForceAtlas2 but this time only the unsupervised nodes were allowed to move. All analyses were performed using the open source Scaffold maps R package available at GitHub.

Statistical Scaffold Maps

To identify changes in the tumor microenvironment during immune-mediated rejection, an effort was made to systematically define changes in immune cell organization and behavior between effective and ineffective treatments. The effort was aided by a computational method called Scaffold maps for creating a reference map from high-dimensional single-cell data, facilitating comparisons across samples (Spitzer et al., 2015). These maps provided a data-driven representation of the cells present in a sample while also denoting the location of landmark immune cell populations, defined using prior knowledge of the immune system. These Landmarks (which can be visualized as black nodes in a graphic representation) function as flags to orient the investigator. In these graphs, the similarity of two groups of cells was visualized by the length of the edge connecting them. In other words, two groups of cells connected by a short line are similar to one another with respect to the proteins they express.

This method was developed in an extensible manner for future datasets to be incorporated, but it did not enable precise statistical comparisons across groups of samples. Another algorithm for mass cytometry analysis, i.e., Citrus (Bruggner et al., 2014), provided statistical comparisons between groups. The results from Citrus, however, were cumbersome to interpret. Therefore, it was determined whether the statistical inference integrated into Citrus could instead be applied to Scaffold maps. This hybrid method was termed a "Statistical Scaffold". The first step of Scaffold maps was altered, clustering data from all tumor specimens together to define cell groups in an unbiased manner. This enabled direct comparisons across samples. The Significance Analysis of Microarrays framework was then used to identify statistically significant features between the sample types (effective versus ineffective treatment groups) as in Citrus (Bair and Tibshirani, 2004; Bruggner et al., 2014). The resulting Scaffold maps were then colored by statistical significance, where features with q-values less than 0.05 (adjusted for multiple testing) were colored in either red or blue depending on the directionality of the change (for example, up or down in the group that received effective therapy). These features can either be changes in the frequency or molecular expression of a particular cell subset.

Cell Population Expression Profiles

Cell clusters of interest were further investigated by visualizing the distribution of protein expression within the cells comprising each cluster as a histogram. This was performed using the density visualization feature of the Scaffold maps R package. Histograms were created by exporting clusters as .FCS files using the Scaffold maps R package and using the flowCore and ggplot2 packages in R to write vector histogram plots. Scripts are available at github, using mhspitzer as an identifier.

Unsupervised Force-Directed Graph Generation

Cells were manually gated as Live CD45+ lineage- (Ter119, Ly6G, Siglec-F, CD19, B220, F4/80, CD11c, PDCA-1, FcεR1α) and then CD3+ to identify T cells. The gated cell populations for each tissue/timepoint/treatment group were clustered independently in 50 clusters using clara in R. The clusters for all the tissues were combined in a single graph with edge weights defined as the cosine similarity between the vectors of median marker values of each cluster. All the pairwise distances were calculated and for each node only the 10 edges of highest weight were retained. The graph was then laid out using the ForceAtlas2 algorithm in Gephi (https://gephi.org).

Correlation Network Analysis and Connectivity Analysis

Immune cell subsets were gated from mass cytometry data, and the frequency of each subset in the peripheral blood samples was calculated. Pairwise Spearman correlations were calculated for each immune cell subset, and hierarchical clustering was performed to organize the correlation matrix. The hierarchical clustering result was additionally imposed on the correlation matrix as a means of comparing the networks.

For the connectivity analysis, an adjacency matrix was created from the correlation matrix of animals receiving effective therapy, using a Spearman correlation coefficient of 0.5 as the threshold. The number of remaining correlations was tabulated for each immune cell population from each tissue, and these were rank ordered. The graph of the adjacency matrix visualizes all positive and negative correlations present in the adjacency matrix for each subset.

Example 2

A CD4 T Cell Subset is Associated with a Favorable Response to Immunotherapy in Melanoma Patients Eligible patients were adults with histologically confirmed unresectable metastatic melanoma as previously reported (Kwek et al., 2015). The protocol was approved by the Institutional Review Board of each participating institution and was conducted in accordance with the ethical principles of the Declaration of Helsinki and within the Good Clinical Practice guidelines as defined by the International Conference on Harmonization. All patients gave written informed consent for participation in the study. The trial was registered at the ClinicalTrials website with Identifier NCTO1363206.

At the initiation of treatment (months 1-3), patients were treated with four cycles of GM-CSF and ipilimumab administered every 3 weeks. Ipilimumab was administered intravenously at a dose of 10 mg/kg on day 1 of each 21-day cycle. GM-CSF was administered subcutaneously daily for 14 days at a dose of 125 mg/m$^2$ beginning on day 1 of each cycle. After the first four cycles of treatment, GM-CSF administration without ipilimumab continued for four more cycles on the same schedule and dose for the first 14 days of every 21-day cycle until month 6. Maintenance therapy began at month 6 and consisted of ipilimumab in the same dose (10 mg/kg) combined with 14 days of GM-CSF. This combination was administered every 3 months thereafter for up to 2 years or until disease progression or unacceptable toxicity.

Blood samples were obtained at week 3 (end of cycle 1) and at week 6 (end of cycle 2) and were cryopreserved for subsequent analysis by flow cytometry. Cell-surface staining was performed in fluorescence-activated cell sorting (FACS) buffer for 30 minutes at 4° C. Intracellular forkhead box P3 (FoxP3) was performed using the FoxP3 fix/perm buffer set (BioLegend, Inc.) according to the manufacturer's protocol. The following anti-human antibodies were used: (Alexa Fluor 700)-CD3 (clone HIT3a), (Brilliant violet 570)-CD4 (clone RPA-T4), (Brilliant violet 650)-CD25 (clone BC96), (Alexa Fluor 647)-CD127 (clone A019D5), (Alexa Fluor 488)-FoxP3 (clone 206D), and (Brilliant violet 421)-PD-1 (clone EH12.2H7). All antibodies were purchased from BioLegend, Inc. Stained cells were fixed with Fluorofix buffer (BioLegend, Inc.) according to manufacturer's instructions and analyzed with an LSR II flow cytometer (BD Biosciences).

Figure 3:
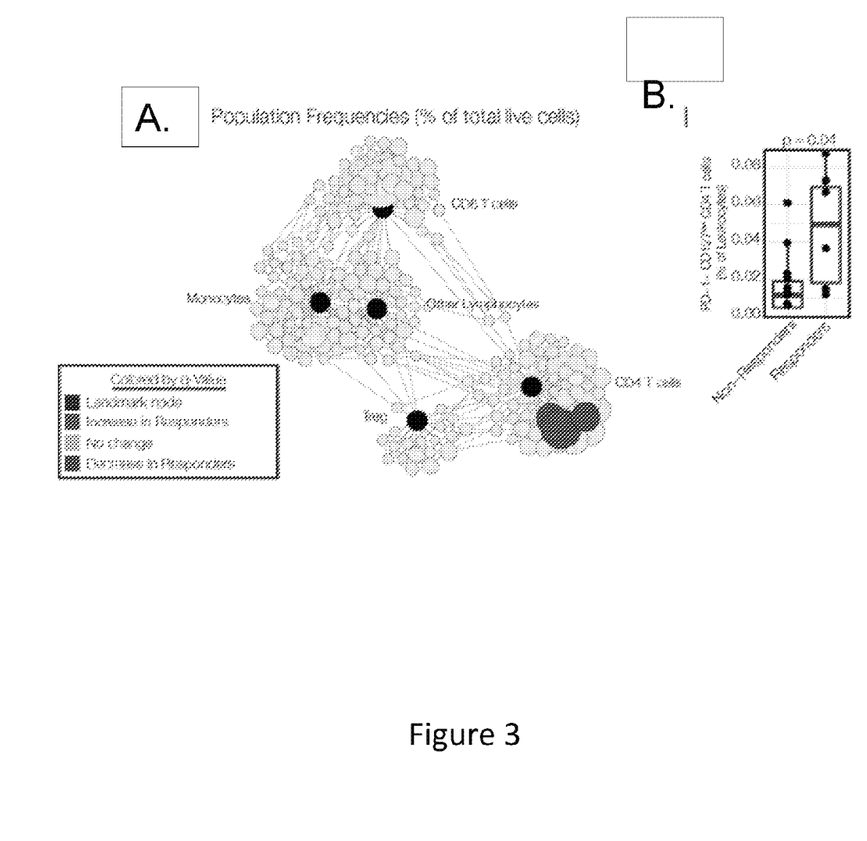
FIG. 3. A CD4 T cell subset from the periphery is sufficient to mediate anti-tumor immunity.
Figure 4:
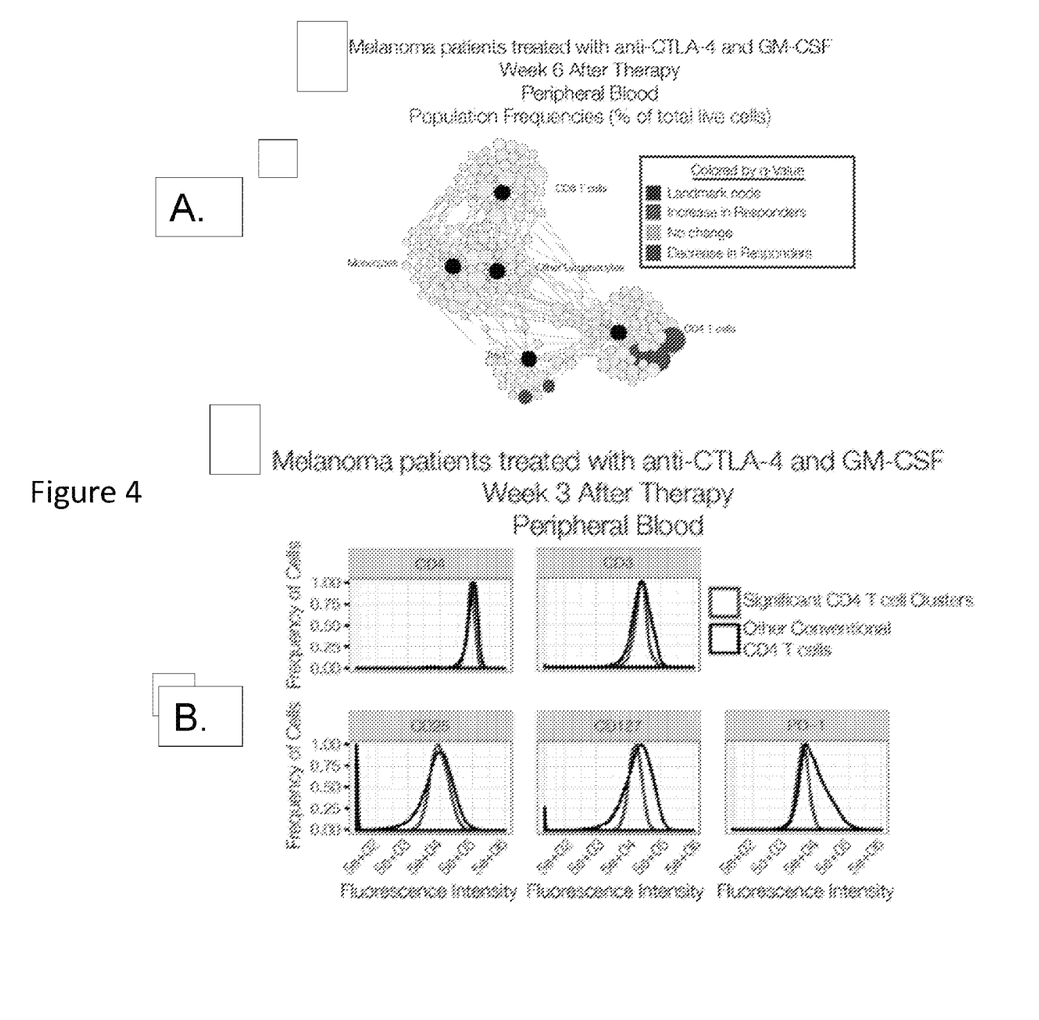
FIG. 4. A CD4 T cell subset from the periphery is sufficient to mediate anti-tumor immunity.

The experiment was conducted to determine whether an effector memory Th1 subset of CD4 T cells that were CD44+CD69+CD62L-CD27$^{low}$ T-bet+, such as CD4 T cells expressing a high level of CD90, could be found in the blood of cancer patients who responded to immunotherapy. A clinical study of melanoma patients who received anti-CTLA-4 antibodies (Ipilimumab) in combination with GM-CSF was recently described (Kwek et al., 2015). Blood from these patients was analyzed both three- and six-weeks post-therapy using Statistical Scaffold. Consistent with preclinical results, specific clusters of CD4 T cells were significantly elevated in responders compared to non-responders at both time points (FIG. 3A). A subset of Tregs was also elevated in responders six weeks after therapy (FIG. 4A). The expanded clusters expressed lower levels of CD127 compared to the remaining CD4 T cells, indicative of activation, and lower levels of PD-1, suggesting that they were not exhausted (FIG. 4B). The results were confirmed by manually gating PD-1$^{low}$ CD127$^{low}$ CD4 T cells (FIG. 3B). A Statistical Scaffold map of blood cells obtained from the melanoma patients is provided in FIG. 3A. The frequency of PD-1$^{low}$ CD127$^{low}$ CD4 T cells relative to total leukocytes is shown in FIG. 3B. These results provide experimental evidence of a critical role for CD4 T cells in coordinating effective anti-tumor immunity in humans, and more particularly, provide experimental evidence for using the PD-1$^{low}$ CD127$^{low}$ CD4 T cell sub-population as a marker for amenability to anti-cancer immunotherapy, providing the convenience of an assay that can be performed on a peripheral blood sample or samples obtained from secondary lymphoid organs (e.g., lymph nodes, spleen) as well as samples obtained from tumors.

REFERENCES

Bair, E., and Tibshirani, R. (2004). Semi-supervised methods to predict patient survival from gene expression data. PLoS Biol. 2, e108.

Bandura, D. R., Baranov, V. I., Omatsky, 0.1., Antonov, A., Kinach, R., Lou, X., Pavlov, S., Vorobiev, S., Dick, J. E., and Tanner, S. D. (2009). Mass cytometry: technique for real time single cell multitarget immunoassay based on inductively coupled plasma time-of-flight mass spectrometry. Anal. Chem. 81, 6813-6822.

Bates, G. J., Fox, S. B., Han, C., Leek, R. D., Garcia, J. P., Harris, A. L., and Banham, A. H. (2006). Quantification of regulatory T cells enables the identification of high-risk breast cancer patients and those at risk of late relapse. J. Clin. Oncol. 24, 5373-5380.

Bendall, S. C., Bendall, S. C., Simonds, E. F., Simonds, E. F., Qiu, P., Qiu, P., Amir, E. A. D., Amir, E.-A. D., Krutzik, P. O., Krutzik, P. O., et al. (2011). Single-Cell Mass Cytometry of Differential Immune and Drug Responses Across a Human Hematopoietic Continuum. Science 332, 687-696.

Bos, P. D., Plitas, G., Rudra, D., Lee, S. Y., and Rudensky, A. Y. (2013). Transient regulatory T cell ablation deters oncogene-driven breast cancer and enhances radiotherapy. J Exp Med 210, 2435-2466.

Broz, M. L., Binnewies, M., Boldajipour, B., Nelson, A. E., Pollack, J. L., Erle, D. J., Barczak, A., Rosenblum, M. D., Daud, A., Barber, D. L., et al. (2014). Dissecting the Tumor Myeloid Compartment Reveals Rare Activating Antigen-Presenting Cells Critical for T Cell Immunity. Cancer Cell 1-15.

Bruggner, R. V., Bodenmiller, B., Dill, D. L., Tibshirani, R. J., and Nolan, G. P. (2014). Automated identification of stratifying signatures in cellular subpopulations. Proc. Natl. Acad. Sci. U.S.A. 111, E2770-E2777.

Bulliard, Y, Jolicoeur, R., Windman, M., Rue, S. M., Ettenberg, S., Knee, D. A., Wilson, N. S., Dranoff, G., and Brogdon, J. L. (2013). Activating Fcγ receptors contribute to the antitumor activities of immunoregulatory receptor-targeting antibodies. J Exp Med 210, 1685-1693.

Carmi, Y, Spitzer, M. H., Linde, I. L., Burt, B. M., Prestwood, T. R., Perlman, N., Davidson, M. G., Kenkel, J. A., Segal, E., Pusapati, G. V., et al. (2015). Allogeneic IgG combined with dendritic cell stimuli induce antitumour T-cell immunity. Nature 1-6.

Chen, D. S., and Mellman, I. (2013). Oncology meets immunology: the cancer-immunity cycle. Immunity 39, 1-10.

Cheng, G., Yuan, X., Tsai, M. S., Podack, E. R., Yu, A., and Malek, T. R. (2012). IL-2 receptor signaling is essential for the development of Klrg1+ terminally differentiated T regulatory cells. J. Immunol. 189, 1780-1791.

Cohen, C. J., Gartner, J. J., Horovitz-Fried, M., Shamalov, K., Trebska-McGowan, K., Bliskovsky, V. V., Parkhurst, M. R., Ankri, C., Prickett, T. D., Crystal, J. S., et al. (2015). Isolation of neoantigen-specific T cells from tumor and peripheral lymphocytes. J. Clin. Invest. 125, 3981-3991.

Coley, W. B. (1893). The treatment of malignant tumors by repeated inoculations of erysipelas: with a report of ten original cases. Am J Med Sci 487-511.

Curiel, T. J., Coukos, G., Zou, L., Alvarez, X., Cheng, P., Mottram, P., Evdemon-Hogan, M., Conejo-Garcia, J. R., Zhang, L., Burow, M., et al. (2004). Specific recruitment of regulatory T cells in ovarian carcinoma fosters immune privilege and predicts reduced survival. Nat Med 10, 942-949.

Dankort, D., Curley, D. P., Cartlidge, R. A., Nelson, B., Karnezis, A. N., Damsky, W. E., Jr, You, M. J., DePinho, R. A., McMahon, M., and Bosenberg, M. (2009). BrafV600E cooperates with Pten loss to induce metastatic melanoma. Nat Genet 41, 544-552.

Finck, R., Simonds, E. F., Jager, A., Krishnaswamy, S., Sachs, K., Fantl, W., Pe'er, D., Nolan, G. P., and Bendall, S. C. (2013). Normalization of mass cytometry data with bead standards. Cytometry A 83, 483-494.

Gabrilovich, D. I., Ostrand-Rosenberg, S., and Bronte, V. (2012). Coordinated regulation of myeloid cells by tumours. Nature Reviews Immunology 12, 253-268.

Haeryfar, S. M. M., and Hoskin, D. W. (2004). Thy-1: More than a Mouse Pan-T Cell Marker. The Journal of Immunology 173, 3581-3588.

Hanninen, A., Maksimow, M., Alam, C., Morgan, D. J., and Jalkanen, S. (2011). Ly6C supports preferential homing of central memory CD8+ T cells into lymph nodes. Eur. J. Immunol. 41, 634-644.

Herbst, R. S., Soria, J. -C., Kowanetz, M., Fine, G. D., Hamid, O., Gordon, M. S., Sosman, J. A., McDermott, D. F., Powderly, J. D., Gettinger, S. N., et al. (2014). Predictive correlates of response to the anti-PD-L1 antibody MPDL3280A in cancer patients. Nature 515, 563-567.

Hodi F S, O'Day S J, McDermott D F, Weber R W, Sosman J A, Haanen J B, et al. Improved survival with ipilimumab in patients with metastatic melanoma. The New England journal of medicine 2010; 363:711-23.

Hodi F S, Lee S, McDermott D F, Rao U N, Butterfield L H, Tarhini A A, et al. Ipilimumab plus sargramostim vs ipilimumab alone for treatment of metastatic melanoma: a randomized clinical trial. JAMA: thejournal of the American Medical Association 2014; 312:1744-53.

Hotson, D., Gopinath, S., Nolan, G. P., and Monack, D. M. (2012). A systems biology approach to persistent Salmonella infection reveals a neutrophil dependent IL-2 mediated dampening of TH1 response. 1-29.

Ideker, T., and Krogan, N. J. (2012). Differential network biology. Mol. Syst. Biol. 8, 1-9.

Im, S. J., Hashimoto, M., Gerner, M. Y, Lee, J., Kissick, H. T., Burger, M. C., Shan, Q., Hale, J. S., Lee, J., Nasti, T. H., et al. (2016). Defining CD8+ T cells that provide the proliferative burst after PD-1 therapy. Nature 1-20.

Jiang, Y., Li, Y., and Zhu, B. (2015). T-cell exhaustion in the tumor microenvironment. Cell Death Dis 6, el 792.

Kantoff, P. W., Higano, C. S., Shore, N. D., Berger, E. R., Small, E. J., Penson, D. F., Redfern, C. H., Ferrari, A. C., Dreicer, R., Sims, R. B., et al. (2010). Sipuleucel-T immunotherapy for castration-resistant prostate cancer. N. Engl. J. Med. 363, 411-422.

Kvistborg, P., Philips, D., Kelderman, S., Hageman, L., Ottensmeier, C., Joseph-Pietras, D., Welters, M. J. P., van der Burg, S., Kapiteijn, E., Michielin, O., et al. (2014). Anti-CTLA-4 therapy broadens the melanoma-reactive CD8+ T cell response. Science Translational Medicine 6, 254ra128-254ra128.

Kwek, S. S., Kahn, J., Greaney, S. K., Lewis, J., Cha, E., Zhang, L., Weber, R. W., Leonard, L., Markovic, S. N., Fong, L., et al. (2015). GM-CSF and ipilimumab therapy in metastatic melanoma: Clinical outcomes and immunologic responses. Oncoimmunology 5, e1101204-e1101211.

Matloubian, M., Lo, C. G., Cinamon, G., Lesneski, M. J., Xu, Y., Brinkmann, V., Allende, M. L., Proia, R. L., and Cyster, J. G. (2004). Lymphocyte egress from thymus and peripheral lymphoid organs is dependent on S1P receptor 1. Nature 427, 355-360.

McDermott D, Lebbe C, Hodi F S, Maio M, Weber J S, Wolchok J D, et al. Durable benefit and the potential for long-term survival with immunotherapy in advanced melanoma. Cancer treatment reviews 2014.

Pelletier, N., McHeyzer-Williams, L. J., Wong, K. A., Urich, E., Fazilleau, N., and McHeyzer-Williams, M. G. (2010). Plasma cells negatively regulate the follicular helper T cell program. Nature hnmunology 11, 1110-1118.

Porter, D. L., Levine, B. L., Kalos, M., Bagg, A., and June, C. H. (2011). Chimeric Antigen Receptor-Modified T Cells in Chronic Lymphoid Leukemia. N. Engl. J. Med. 365, 725-733.

Prieto P A, Yang J C, Sherry R M, Hughes M S, Kammula U S, White D E, et al. CTLA-4 blockade with ipilimumab: long-term follow-up of 177 patients with metastatic melanoma. Clinical cancer research: an official journal of the American Association for Cancer Research 2012; 18:2039-47.

Restifo, N. P., Dudley, M. E., and Rosenberg, S. A. (2012). Adoptive immunotherapy for cancer: harnessing the T cell response. Nature Reviews Immunology 12, 269-281.

Robert C, Thomas L, Bondarenko I, O'Day S, M D J, Garbe C, et al. Ipilimumab plus dacarbazine for previously untreated metastatic melanoma. The New England journal of medicine 2011; 364:2517-26.

Rosenberg, S. A. (2014). Decade in review-cancer immunotherapy: Entering the mainstream of cancer treatment. Nat Rev Clin Oncol 11, 630-632.

Simpson, T. R., Li, F., Montalvo-Ortiz, W., Sepulveda, M. A., Bergerhoff, K., Arce, F., Roddie, C., Henry, J. Y, Yagita, H., Wolchok, J. D., et al. (2013). Fc-dependent depletion of tumor-infiltrating regulatory T cells co-defines the efficacy of anti-CTLA-4 therapy against melanoma. J Exp Med 210, 1695-1710.

Spitzer, M. H., Gherardini, P. F., Fragiadakis, G. K., Bhattacharya, N., Yuan, R. T., Hotson, A. N., Finck, R., Carmi, Y, Zunder, E. R., Fantl, W. J., et al. (2015). An interactive reference framework for modeling a dynamic immune system. Science 349, 1259425- 1259425.

Spranger, S., Koblish, H. K., Horton, B., Scherle, P. A., Newton, R., and Gajewski, (2014). Mechanism of tumor rejection with doublets of CTLA-4, PD-1/PD-L1, or IDO blockade involves restored IL-2 production and proliferation of CD8(+) T cells directly within the tumor microenvironment. Journal for ImmunoTherapy of Cancer 2, 3.

Swain, S. L., McKinstry, K. K., and Strutt, T. M. (2012). Expanding roles for CD4+ T cells in immunity to viruses. Nature Reviews Immunology 12, 136-148.

Topalian, S. L., Drake, C. G., and Pardoll, D. M. (2015). Immune Checkpoint Blockade: A Common Denominator Approach to Cancer Therapy. Cancer Cell 27, 450-461.

Tran, E., Turcotte, S., Gros, A., Robbins, P. F., Lu, -C., Dudley, M. E., Wunderlich, J. R., Somerville, R. P., Hogan, K., Hinrichs, C. S., et al. (2014). Cancer immunotherapy based on mutation-specific CD4+ T cells in a patient with epithelial cancer. Science 344, 641-645.

Wherry, E. J., Ha, S. -J., Kaech, S. M., Haining, W. N., Sarkar, S., Kalia, V, Subramaniam, S., Blattman, J. N., Barber, D. L., and Ahmed, R. (2007). Molecular Signature of CD8+ T Cell Exhaustion during Chronic Viral Infection. Immunity 27, 670-684.

Xie, Y, Akpinarli, A., Maris, C., Hipkiss, E. L., Lane, M., Kwon, E. -K. M., Muranski, P., Restifo, N. P., and Antony, P A. (2010). Naive tumor-specific CD4+ T cells differentiated in vivo eradicate established melanoma. Journal of Experimental Medicine 207, 651-667.

Zunder, E. R., Finck, R., Behbehani, G. K., Amir, E. -A. D., Krishnaswamy, S., Gonzalez, V. D., Lorang, C. G., Bjornson, Z., Spitzer, M. H., Bodenmiller, B., et al. (2015). Palladium-based mass tag cell barcoding with a doublet-filtering scheme and single-cell deconvolution algorithm. Nat Protoc 10, 316-333.

Each of the references cited herein is incorporated by reference herein in its entirety, or in relevant passage, as would be apparent from the context of its citation.

From the disclosure it will be appreciated that, although specific embodiments of the invention have been described herein for purposes of illustration, various modifications may be made without deviating from the spirit and scope of the invention. All references, issued patents and patent applications cited within the body of the instant specification are hereby incorporated by reference in their entirety, for all purposes. It must be noted that, as used in the specification and the appended claims, the singular forms "a," "an" and "the" include plural referents unless the context clearly dictates otherwise.

What is claimed is:

1. A method of treating cancer in a human subject having cancer comprising:
    (a) generating a first scaffold map from a first population of blood leukocytes isolated from the human subject having cancer, wherein the cancer is melanoma, and a second scaffold map from a second population of blood leukocytes isolated from a control, wherein the control is the human subject having cancer at an earlier time, a distinct human subject having cancer that is unresponsive to anti-cancer immunotherapy, or a healthy human subject, wherein the cancer is melanoma;
    (b) generating a first cell population expression profile from the first scaffold map, and a second cell population expression profile from the second scaffold map;
    (c) comparing the first cell population expression profile and the second cell population expression profile to determine expression level of $CD127^{low}$ $PD-1^{low}$ T cells in the human subject having cancer and the control;
    (d) administering a therapeutically effective amount of a composition comprising an immune checkpoint inhibitor, wherein the immune checkpoint inhibitor is ipilumimab, to the human subject having cancer, if the expression level of $CD127^{low}$ $PD-1^{low}$ T cells in the human subject having cancer is greater than the expression level of $CD127^{low}$ $PD-1^{low}$ T cells in the control, thereby treating the cancer in the human subject having cancer.

2. The method of claim 1, further comprising administering a soluble growth factor to the human subject having cancer.

3. The method of claim 2, wherein the soluble growth factor is granulocyte-macrophage colony stimulating factor (GM-CSF).

4. The method of claim 1, wherein the T cells are CD4 positive cells.

5. The method of claim 4, wherein the CD4 positive cells are regulatory T cells.

6. The method of claim 1, wherein the control is the human subject having cancer at an earlier time.

7. The method of claim 6, wherein the earlier time is prior to a cancer treatment.

8. The method of claim 1, wherein the human subject having cancer has a tumor and the first population of blood leukocytes is obtained intratumorally.

9. The method of claim 1, wherein the first population of blood leukocytes is obtained from a secondary lymphoid organ or from peripheral blood.

10. The method of claim 1, wherein the immune checkpoint inhibitor inhibits the growth of cancer cells.

11. The method of claim 1, wherein the immune checkpoint inhibitor inhibits the migration of cancer cells.

12. The method of claim 1, wherein the generating a first and second scaffold map comprises obtaining, from a third party, a dataset comprising data representing the level(s) of $CD127^{low}$ $PD-1^{low}$ cells.

13. The method of claim 1, wherein the generating a first and second scaffold map comprises processing, using flow cytometry, a sample from the human subject having cancer and/or control to experimentally determine a dataset comprising data representing the level(s) of $CD127^{low}$ $PD-1^{low}$ cells.

14. The method of claim 5, wherein the CD4 positive cells are $CD4^+CD25^+$ regulatory T cells.

\* \* \* \* \*